(12) United States Patent
Ralph et al.

(10) Patent No.: US 6,689,134 B2
(45) Date of Patent: *Feb. 10, 2004

(54) LONGITUDINAL PLATE ASSEMBLY HAVING AN ADJUSTABLE LENGTH

(75) Inventors: James D. Ralph, Seaside Park, NJ (US); Stephen Tatar, Montvale, NJ (US)

(73) Assignee: Third Millennium Engineering, LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/092,893

(22) Filed: Mar. 7, 2002

(65) Prior Publication Data

US 2003/0153920 A1 Aug. 14, 2003

Related U.S. Application Data

(63) Continuation of application No. 10/075,689, filed on Feb. 13, 2002.

(51) Int. Cl.[7] ................................................ A61B 17/56
(52) U.S. Cl. .............................. 606/71; 606/69; 606/70
(58) Field of Search ............................ 606/71, 70, 69, 606/65, 57, 53, 54, 58, 105

(56) References Cited

U.S. PATENT DOCUMENTS

| 2,486,303 | A | * | 10/1949 | Longfellow | 606/71 |
|---|---|---|---|---|---|
| 4,157,715 | A | * | 6/1979 | Westerhoff | 606/60 |
| 5,484,439 | A | * | 1/1996 | Olson et al. | 606/65 |
| 5,520,690 | A | * | 5/1996 | Errico et al. | 606/61 |
| 5,531,747 | A | * | 7/1996 | Ray | 606/61 |
| 5,616,142 | A | * | 4/1997 | Yuan et al. | 606/61 |
| 5,672,177 | A | * | 9/1997 | Seldin | 606/71 |
| 6,402,756 | B1 | * | 6/2002 | Ralph et al. | 606/71 |

* cited by examiner

*Primary Examiner*—Pedro Philogene
(74) *Attorney, Agent, or Firm*—Joseph P. Errico, Esq.; Timothy J. Bortree, Esq.

(57) ABSTRACT

An orthopedic device including a longitudinal plate assembly having an adjustable length and two ends. Each of the ends includes a feature that can be used to couple the end to a body structure, such as, for example, a vertebral bone. Preferably, the assembly includes two longitudinal plates that can translate longitudinally with respect to one another through a plurality of positions and be secured with respect to one another at one of the positions, thereby enabling the length of the assembly to be adjusted. Inasmuch as the length of the plate assembly can be adjusted, the surgeon can set the length to the most clinically appropriate length for effective coupling of the plate assembly to the body structure.

19 Claims, 7 Drawing Sheets

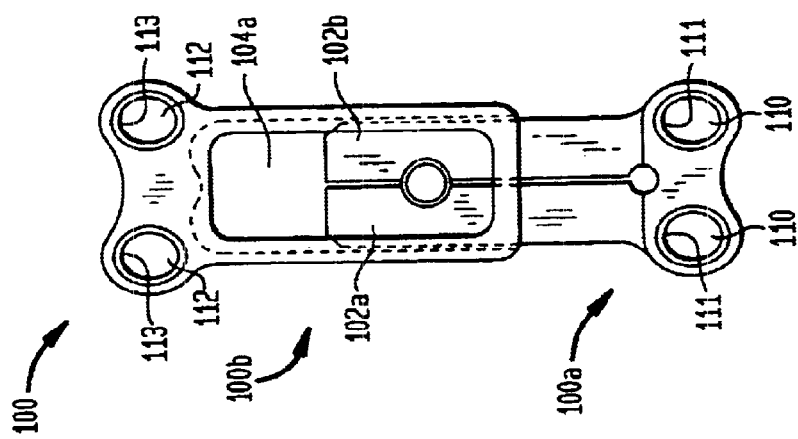
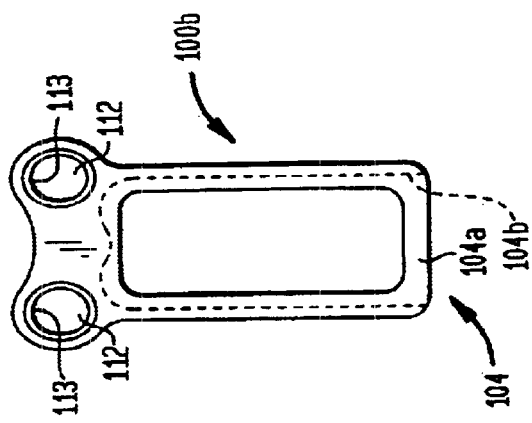
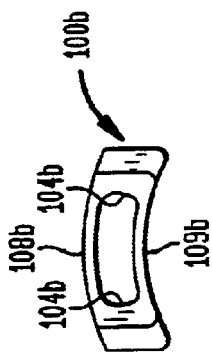
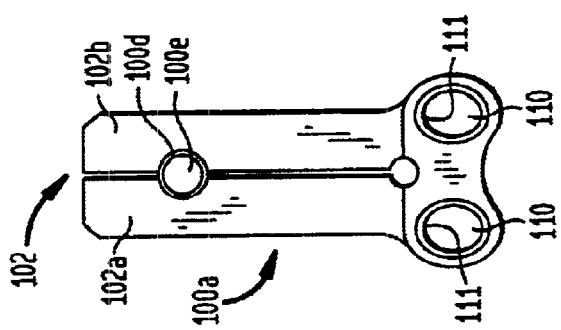
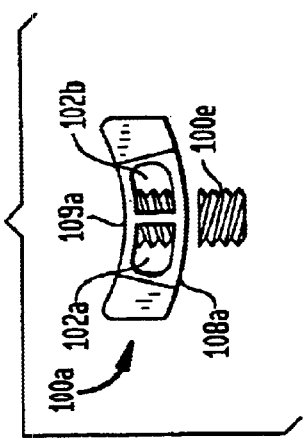

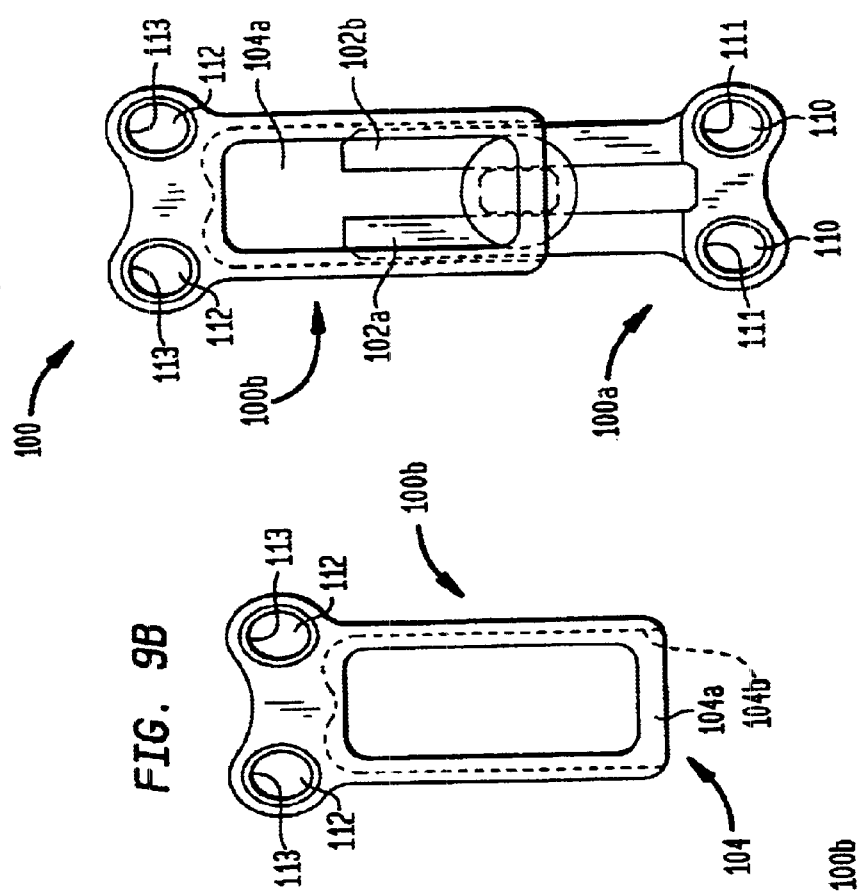

LONGITUDINAL PLATE ASSEMBLY HAVING AN ADJUSTABLE LENGTH

CROSS REFERENCE TO RELATED APPLICATION

The present application is a continuing application of U.S. Ser. No. 10/075,689 filed Feb. 13, 2002 entitled "Longitudinal Plate Assembly Having An Adjustable Length".

FIELD OF THE INVENTION

The invention relates generally to a spinal implant assembly for holding vertebral bones fixed relative to one another. More particularly, the invention relates to a longitudinal plate assembly having an adjustable length and two ends that each can be coupled to a body structure, such as a vertebral bone, for use in surgical procedures for stabilizing the relative motion of, or permanently immobilizing, the body structures.

BACKGROUND OF THE INVENTION

The bones and connective tissue of an adult human spinal column consists of more than twenty discrete bones coupled sequentially to one another by a tri-joint complex which consist of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine includes the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Referring now to FIGS. 1 and 2, a typical vertebral body is shown in a top view and a side view. The spinal cord is housed in the central canal 10, protected from the posterior side by a shell of bone called the lamina 12. The lamina 12 has three large protrusions, two of which extend laterally from the shell and are referred to as the transverse process 14. The third extends back and down from the lamina and is called the spinous process 16. The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14, 16.

The spinal column of bones is highly complex in that it includes over twenty bones coupled to one another, housing and protecting critical elements of the nervous system which have innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and disease are a few of the causes which can result in spinal pathologies for which permanent immobilization of multiple vertebral bodies may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determine the appropriate surgical protocol and implantation assembly. The use of screw plate assemblies for stabilization and immobilization via lateral or anterior entrance is, however, common.

Because spinal injuries vary with regard to the number of vertebral bodies affected, the proximity of the affected vertebral bodies with respect to one another, and the proximity of the unaffected or stable vertebral bodies with respect to one another, it is necessary for the treatment of a given spinal injury to use a plate assembly having a length that can be used effectively to immobilize, with respect to one another, those vertebral bodies that must be so immobilized to achieve clinically desirable results. For example, depending on the spinal injury, it may be necessary to immobilize two adjacent vertebral bodies. Or, for example, it may be necessary to immobilize two vertebral bodies on either side of one or more unstable or damaged vertebral bodies. Potentially, each spinal injury therefore requires a plate assembly having a different length.

In addition, the vertebral bodies of the spine are not all equal in length or identical in shape. Some are smaller than others, and are therefore shorter and, for example, have smaller transverse processes, spinous processes, and/or smaller pedicles. Therefore, depending on the location of the spinal injury along the spine, it is again necessary to select a plate assembly having a length that can be used effectively to immobilize, with respect to one another, those vertebral bodies that must be so immobilized to achieve clinically desirable results. For example, in the cervical portion of the spine, the immobilization of two adjacent vertebral bodies will require a plate assembly of a given length, while the immobilization of two adjacent vertebral bodies in the lumbar region will typically require a plate assembly that is longer. And, of course, the selection of the plate assembly of appropriate length must take into account the specific location of the bone structures to which the a plate assembly will be coupled, as these specific locations vary depending on the spinal injury and the damage caused thereby.

Further, because the spine is routinely subject to high loads which cycle during movement, one of the primary concerns of physicians performing spinal implantation surgeries, as well as of the patients in whom the implants are placed, is the risk of screw pull-out. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for a pair of screws which are angled inward, "toe nailed", or ones which diverge within the bone, the amount of bone which must fail increases substantially as compared to pairs of screws which are implanted in parallel along the axis that the loading force is applied. It has, therefore, been an object of those in the art to provide a screw plate assembly which permits the screws to be entered into the vertebral body at angles other than 90 degrees.

A great concern, however, with screws being implanted in the anterior portion of the spine, most particularly in the cervical spine, is that there are important internal tissue structures which, because of their proximity to the implant, may be damaged by a dislocated screw. In the cervical spine, the esophagus is located directly in front of the anterior surface of the vertebral body, and therefore, in potential contact with an implanted cervical plate assembly. Breaches of the esophageal wall permit bacterial contamination of the surrounding tissues, including the critical nerves in and around the spinal cord. Such contamination can be fatal. Because screw pull-out represents one of the largest risks of esophageal perforation, it has been an object of those in the art to produce a cervical screw plate assembly having a locking means which couples, not only the plate assembly to the bone, but locks the screw to the plate assembly. In such a design, it is intended that, even if the bone holding the screw fails, the screw will not separate from the plate assembly.

In addition to pull-out, however, it has been observed that if the screw plate assembly includes screw heads which protrude beyond the exterior surface of the plate assembly, long term wearing of surrounding tissues may occur, leading to the development of abscesses and holes, which, once again, can have grave consequences. With respect to cervical plate assemblies, which are necessarily thin, on the order of a few millimeters, unless the system is designed to specifically accommodate non-perpendicular screw-in directions, the heads of the screws which are desirably toe-nailed in are a considerable risk.

Similar concerns exist in the thoracic and lumbar regions with respect to anterior and lateral fixation implants as their are proximally located organs as well as a plurality of major blood vessels which may be compromised by either catastrophic screw pull-out and/or long term wearing of non-flush surface protrusions.

One screw plate design which has been offered to provide physicians and patients with a reduced risk of pull-out or damage to proximal tissues is the Orion™ Anterior Cervical Plate System of Sofamor Danek USA, 1800 Pyramid Place, Memphis, Tenn. 38132. The Orion™ system teaches a plate having two pair of guide holes through which the screws are inserted to fix the plate to the vertebral body. The plate further includes external annular recessions about each of the guide holes which are radially non-symmetric in depth. More particularly, the annular recessions serve as specific angle guides for the screws so that they may be inserted non-perpendicularly with respect to the overall curvature of the plate. In addition, the Orion™ plate includes an additional threaded hole disposed between each of the pairs of guide holes so that a corresponding set screw may be inserted to lock the bone screws to the plate.

Although the Orion™ system achieved certain advantages over prior cervical screw plate assemblies, it is not without failures. Specifically, a given plate can accommodate only one screw-in angulation per hole, preferably in accordance with the angle of the annular recession. This is undesirable, in that physicians often must inspect the vertebral bodies during the implantation procedure before making the decision as to which screw-in angle is the ideal. By forcing the physician to chose from a limited set of angles, it is unavoidable that physicians will be forced to implant plates having screws which were positioned non-ideally. While providing a variety of plates having different angle guide holes and annular recession orientations is possible, the complexity and expense of providing a full spectrum of plates available in the operating room for the surgeon to choose from is undesirable. It is a failure of the system that one plate cannot accommodate a variety of different screw-in angles.

It is an additional failure of the system that an extra set screw is required to lock the screw to the plate. Plates for use in the cervical spine are very thin, and if the screw head already rests in an annular recess, and there is to be enough room for the head of the set screw to rest on top of the head of the bone screw, the thickness of the remaining plate must be reduced even further. The thinner the plate is at the load bearing points—the guide holes—the weaker the plate is overall.

It is a further failure of the system that one plate cannot accommodate a variety of lengths. Specifically, a given plate can accommodate only one length, preferably the length that is needed for the specific injury. This is undesirable, in that physicians often must inspect the vertebral bodies during the implantation procedure before making the decision as to which plate length is the ideal. By forcing the physician to chose from a limited set of lengths, it is unavoidable that physicians will be forced to implant plates having a length that is non-ideal for the application. This problem is compounded by the limited set of angles discussed above, in that the physician may be forced to use an angle other than the one most clinically appropriate simply because the fixed length of the plate, while being the closest clinically appropriate length available, is slightly too long or too short to allow the desired angle to be used. While providing a variety of plates having different lengths is possible, the complexity and expense of providing a full spectrum of plates available in the operating room for the surgeon to choose from is undesirable.

While the preceding discussion has focused on a specific cervical screw plate system and its failures, the same failures apply to the art of vertebral immobilizing screw plate systems which are presently available as well. There are no presently available screw plate assemblies which present a flush surface and provide for means of preventing both screw pull-out from the bone and screw backout from the plate, while simultaneously providing for a wide range of angulation for the bone screws and for a wide range of plate lengths.

An additional concern for physicians who implant screw plates for spinal fixation is proper alignment for pre-drilling of the holes into which the bone screws are driven to hold the plate. As suggested above with respect to the angulation of the annular recesses of the Orion™ system, the process of forming the holes generally involves placing the plate against the appropriate vertebral bodies and using a guide to hold the proper angle with respect to the plate and bone as a drill is used. The difficulty in this process involves slippage at the interface between the unsecured plate and the bone. To avoid slippage, the surgeon is generally required to use, simultaneously, a plate holding mechanism, which may be removably affixed to the plate, to maintain the plate in its proper position, a drill guide to set the desired angulation (which is set by the thread angle of the plate), and the drill itself. It is understood that simultaneous manipulation of these three tools by the surgeon is tedious and difficult.

Therefore, there is a need for a new and novel cervical, thoracic, and/or lumbar screw plate assembly having a polyaxial coupling of the screw to the plate assembly, whereby a single plate assembly is compatible with a wide range of screw-in angles and a wide range of plate assembly lengths. There is also a need for a screw plate assembly having a flush exterior while being fixed to the vertebral bodies which it immobilizes, having no screw head protrusion despite non-perpendicular angulation. There is also a need for a spinal implant assembly which is more sturdy and more versatile than previous designs. There is also a need for a screw plate assembly which provides the surgeon with the greatest freedom to choose the most desirable angle in which to direct the bone screw. There is also a need for an orthopedic screw plate assembly which has a simple and effective locking mechanism for locking the bone screw to the plate assembly. There is also a need for an orthopedic screw plate assembly which has a simple and effective means of holding the plate assembly in position for the pre-drilling of screw holes.

SUMMARY OF THE INVENTION

The invention provides an orthopedic device including a longitudinal plate assembly having an adjustable length and two ends. Each of the ends includes a feature that can be used to couple the end to a body structure, such as, for example, a vertebral bone. Preferably, the assembly includes two longitudinal plates that can translate longitudinally with respect to one another through a plurality of positions and be secured with respect to one another at one of the positions, thereby enabling the length of the assembly to be adjusted. Inasmuch as the length of the plate assembly can be adjusted, the surgeon can set the length to the most clinically appropriate length for effective coupling of the plate assembly to the body structure or structures.

In an embodiment, the invention provides a plate assembly including a first longitudinal plate having an end defined by longitudinal prongs; a second longitudinal plate having a longitudinal bore, the longitudinal bore being adapted to receive the prongs for longitudinal translation therein through a plurality of positions; and a lock assembly for locking the prongs within the bore at one of the positions. Each plate comprises a feature that can be used to couple the plate to a body structure.

In an aspect, the bore has an inner surface and the lock assembly presses the prongs against the inner surface. Preferably, the prongs are laterally adjacent one another and the lock assembly separates the prongs to press them against the inner surface. The lock assembly can include a threaded bore and a set screw passing between the prongs and into the threaded bore. Alternatively, the lock assembly can include a cam that when placed in a first position, does not press the prongs against the inner surface, allowing the prongs to longitudinally translate freely within the bore through the plurality of positions, and when placed in a second position (e.g., rotated 90 degrees with respect to the first position), separates the prongs to press them against the inner surface, preventing longitudinal translation of the prongs within the bore.

In another aspect, a lateral curvature is imparted to the plate assembly. The lateral curvature is preferably contoured to the curved roughly cylindrical surface of the vertebral bodies to which it can be secured.

In yet another aspect, at least one of the features comprises a through hole. Preferably, each feature comprises a pair of through holes. Preferably, there are two threaded holes at each end of the plate assembly extending through the plate assembly, positioned so that they are aligned in pairs with the vertebral bodies to which the plate assembly is to be attached.

In this aspect, the assembly can further include a bone screw having a shaft that can be inserted into the through hole and into a bone. The shaft can be threaded to cooperate with the threading in the through holes. The threading and shaft portion of the bone screws may be of a variety of standard designs, or a particular design which may be found more secure than the standard ones. Preferably, the head is not standard in that it comprises a semi-spherical section.

In this aspect, the assembly can further include a coupling element that has a semi-spherical interior volume and that can be inserted into the through hole. The bone screw can have a semi-spherical head that can be rotationally freely mounted within the semi-spherical interior volume prior to insertion of the coupling element into the through hole. The shaft and the coupling element can be inserted into the through hole and the shaft can be inserted into the bone at a selected angle within a predetermined range of angles, including non-perpendicular angles, relative to the respective plate, thereby locking the coupling element and the head to the respective plate at the selected angle as the head and the coupling element are advanced into the through hole. For example, the first step in a process of implanting such an embodiment of the invention is to position the plate assembly against the vertebral bodies and to align the entry points for the screws. The next step in such a process is to pre-drill holes into the vertebral bones at desired angles, into which the screws will be inserted. With the plate assembly in place, the screws may be screwed into the drilled holes in the vertebral bodies.

In this aspect, the head of the bone screw can have a recess to which a screwdriving tool can be mated for inserting the screw into the through hole and into the bone. The recess can be a slot, phillips, star, hexagonal or other shape that is ideally suited for mating to an appropriate screwdriving tool. When the head of the bone screw is semi-spherical for use with a coupling element in the manner described above, however, the recess should not alter the semi-spherical shape of the head.

Accordingly, the coupling element can have a top surface recess through which the screwdriving tool may be inserted. The top surface recess can be aligned with the recess in the head of the bone screw. This allows the bone screw to be inserted into the bone using the screwdriver. Alternatively, instead of a recess, the coupling element may be partially opened so that the screw and the coupling may be manipulated easily so that the recess in the head of the screw is accessible. In either variation, once the screw has been fully inserted into the vertebral bone, at the desired angle, the coupling element, via its rotationally free mating of the socket to the inserted screw, is realigned so that it may be locked down into the plate assembly. Screwing down the coupling element provides the locking of the screw to the plate assembly, whereby the screw can be angled non-perpendicularly (or perpendicularly, if desired) with respect to the plate assembly, while the coupling element is flush with a bottom surface of one of the plates of the plate assembly, without the need for a set screw.

In this aspect, the interior semi-spherical interior volume of the coupling element can be defined by a curved interior surface which forms a receiving socket into which the semi-spherical head is inserted, whereby the head is rotationally freely mounted in the semi-spherical interior volume. The curved interior surface can include slots which permit the interior semi-spherical volume to expand to facilitate the insertion of the semi-spherical head of the bone screw therein. The through hole can be tapered inwardly to cause, upon insertion of the coupling element into the through hole, the slots to be compressed, which causes the curved interior surface to lock the semi-spherical head of the screw at a definite insertion angle. Therefore, the coupling element may be crush-locked to the head of the screw by the application of a radial force. The tapering has the effect of applying a radial force to the slotted socket portion of the coupling element. This circumferential reduction has the desirable effect of locking the screw at the insertion angle. In this way, the coupling element serves as an additional support for keeping the screw in the vertebral bone at the proper angle.

It is understood that variations in the coupling element (with respect to its recessed or open top) can be used without departing from the scope of the invention so that polyaxial screws may be used with cervical, thoracic, and lumbar plates, despite the considerable variation in plate thicknesses.

In still another aspect, at least one of the plates has a bottom surface and the assembly further includes at least one feature protruding from the bottom surface for removable and temporary fixation of the plate assembly to the body structure. Preferably, the feature comprises a spike. The spike can interface with the vertebral bones to hold the plate assembly in position during the pre-drilling step. For example, the plate assembly may be held firmly in place by simply positioning the plate assembly and applying enough pressure to drive the spikes into the vertebral bone. The spikes will hold the plate assembly in position, thereby freeing the hands of the surgeon to easily and accurately pre-drill the ideally angled holes. The spikes also provide supplementary gripping and holding strength for the plate assembly, in addition to the screws, once the plate assembly has been implanted securely.

BRIEF DESCRIPTION OF THE DRAWINGS

FIG. 3a is a top view of a first plate of an embodiment of the invention.

FIG. 3b is a top view of a second plate of an embodiment of the invention.

FIG. 3c is an end view of a first plate of an embodiment of the invention.

FIG. 3d is an end view of a second plate of an embodiment of the invention.

FIG. 4 is a top view of cooperating first and second plates of an embodiment of the invention.

FIG. 9a1 is a top view of a first plate of a second embodiment of the invention showing prongs closed.

FIG. 9a2 is a top view of a first plate of a second embodiment of the invention showing prongs open.

FIG. 9b is a top view of a second plate of a second embodiment of the invention.

FIG. 9c is an end view of a first plate of a second embodiment of the invention.

FIG. 9d is an end view of a second plate of a second embodiment of the invention.

FIG. 10 is a top view of cooperating first and second plates of a second embodiment of the invention.

DETAILED DESCRIPTION OF THE PREFERRED EMBODIMENTS

Figure 1:
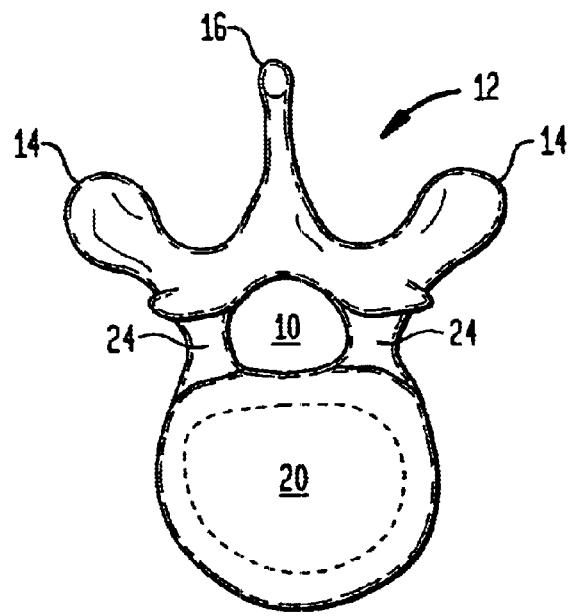
FIG. 1 is a top view of a vertebral bone, the stabilization of which an embodiment of the invention is directed.

While the invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the invention and not as limiting of such broad scope. Like numbers refer to similar features of like elements throughout.

FIGS. 3a, 3b, 3c, 3d and 4, illustrate elements of a plate assembly 100 of an embodiment of the invention. FIG. 3a illustrates a top view of a first longitudinal plate 100a of the plate assembly 100. The first plate 100a has an end 102 defined by longitudinal prongs 102a, 102b that are laterally adjacent one another. While two prongs are shown in this embodiment, and are shown as laterally adjacent one another, it is understood that a greater number of prongs and/or prongs that are adjacent one another in other configurations can be used without departing from the scope of the invention.

FIG. 3b illustrates a top view of a second longitudinal plate 100b of the plate assembly 100. The second plate 100b has an end 104 that has a longitudinal bore 104a that is adapted to receive the prongs 102a, 102b for longitudinal translation therein through a plurality of positions. FIG. 4 illustrates a top view of the plate assembly 100 when the prongs 102a, 102b of the first plate 100a are received within the bore 104a of the second plate 100b. The prongs 102a, 102b can be inserted into the bore 104a and translated longitudinally therein through one or more of the plurality of positions until the desired length of the plate assembly 100 is achieved by stopping the translation at one of the positions, such position establishing the desired relative position of the first plate 100a to the second plate 100b to achieve the desired length of the plate assembly 100.

The plates 100a, 100b may be constructed of any suitably biocompatible material which has the structural strength and durability to withstand the cyclical loading associated with long term fixation to the spine. Materials which would be suitable for such applications include titanium alloys and steels. A specific titanium material which has been utilized in implants of the prior art include ASTM F-136 titanium alloy (Ti 6AL-4V). This material has enhanced mechanical properties including fatigue endurance and tensile strength, as compared with pure titanium.

In order to secure the plates 100a, 100b in the selected position, the plate assembly 100 further includes a lock assembly for locking the prongs 102a, 102b within the bore 104a at the selected position. Activation of the lock assembly secures the relative position of the plates 100a, 100b so that the desired length of the plate assembly 100 is fixed.

FIG. 3c illustrates an end view of the first plate 100a. In this embodiment, as shown in FIG. 3c, the lock assembly includes a threaded bore 100d between the prongs 102a, 102b and a set screw 100e passing between the prongs 102a, 102b and into the threaded bore 100d. Rotation of the set screw 100e advances the set screw 100e into the threaded bore 100d, causing the prongs 102a, 102b to separate as the set screw 100e passes between them as it advances. Preferably, a head of the set screw 100e includes a recess that can be mated with a screwdriving tool and the screwdriving tool can be used to rotate the set screw 100e within the threaded bore 100d to advance the set screw 100e until the prongs 102a, 102b separate.

FIG. 3d illustrates an end view of the second plate 100b. It can be seen that the bore 104a has an inner surface 104b.

FIG. 4 illustrates a plan view of the plate assembly 100 when the prongs 102a, 102b are received within the bore 104a. The prongs 102a, 102b are laterally adjacent one another and the lock assembly separates the prongs 102a, 102b to press them against the inner surface 104b as described above. The compression of the prongs 102a, 102b against the inner surface 104b secures the position of the plates 100a, 100b relative to one another, thereby fixing the length of the plate assembly 100.

FIGS. 9a1, 9a2, 9b, 9c, 9d and 10 will now be discussed as describing a second embodiment of the present invention that is similar to the first embodiment shown in FIGS. 3a–d and 4 in all material respects (and like elements are accordingly like numbered in FIGS. 9a1, 9a2, 9b, 9c, 9d and 10) except that this second embodiment has a different lock assembly. The discussion will then continue with respect to other aspects of the present invention, which apply to both embodiments, except where specifically noted.

Figure 2:
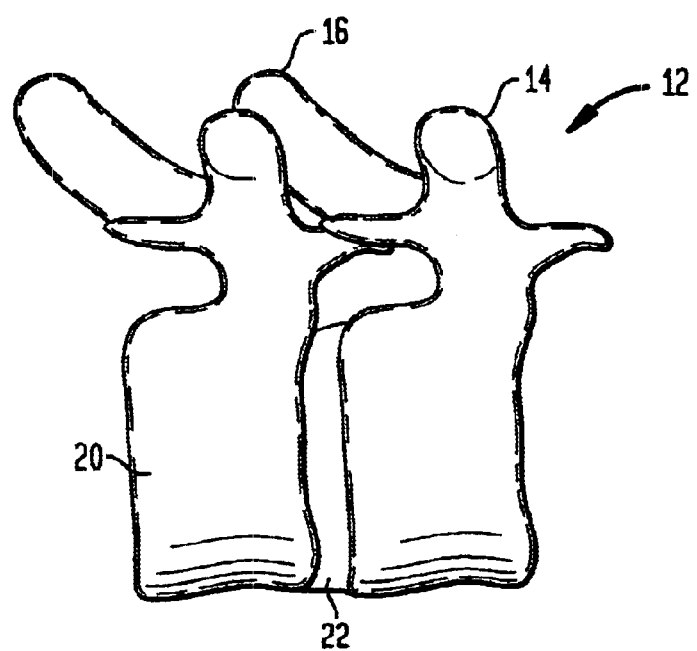
FIG. 2 is a side view of sequentially aligned vertebral bones.

FIG. 9c illustrates an end view of the first plate 100a of the second embodiment, in which the lock assembly includes a cam assembly having a cam 900 that when placed in a first position (e.g., as shown in FIG. 9a1 which is a plan view of the plate assembly 100 of this second embodiment), does not press the prongs 102a, 102b against the inner surface 104b, allowing the prongs 102a, 102b to longitudinally translate freely within the bore 104a through a plurality of positions, and when placed in a second position (e.g., rotated 90 degrees with respect to the first position as shown in FIG. 9a2 which is a plan view of the plate assembly 100 of this second embodiment), separates the prongs 102a, 102b to press them against the inner surface 104b, preventing longitudinal translation of the prongs 102a, 102b within the bore 104a.

For example, a suitable cam 900 would have an elongated cross-section at that portion 908 of the cam 900 that engages the prongs 102a, 102b for separation, such that, e.g., the width of the cam 900 at that portion 908 is smaller than the resting distance between the prongs 102a, 102b (the distance between the prongs 102a, 102b when they are not engaged by the cam 900), and the length of the cam 900 at that portion 908 is greater than the combination of the resting distance between the prongs 102a, 102b and the resting distances between each prong 102a, 102b and the inner surface 104b (the distances between the prongs 102a, 102b and the inner surface 104b when the prongs 102a, 102b are not engaged by the cam 900).

Also, for example, a suitable cam 900 would have at least one feature that maintains the cam 900 within the plate assembly 100. One example of a suitable feature comprises flanges 906 that prevent the cam 900 from slipping out from between the prongs 102a, 102b. Preferably, the flanges 906 have a greater cross-section than the length of the portion 908 of the cam 900, as shown. Another example of a suitable feature comprises a rotatable mounting 902 of the cam 900 to the second plate 100b and such that the cam 900 is located between the prongs 102a, 102b when the prongs 102a, 102b are longitudinally translated in the bore 104a. Although it need not be in some embodiments, such a cam 900 could be made longitudinally translatable in the bore 104a, e.g., on a track, so that it can be slid between the prongs 102a, 102b to any desired location therebetween, and so positionable at any desired prong separation location suitable for the length to which the plate assembly 100 has been adjusted. The mounting to the second plate 100b would also serve to maintain the cam 900 within the plate assembly 100, and therefore would not require the cam 900 to have flanges 906 to maintain it within the plate assembly 100.

Accordingly, when the cam 900 is in the first position, it preferably can be slid between the prongs 102a, 102b to any desired location therebetween, and so is positionable at any desired prong separation location suitable for the length to which the plate assembly 100 has been adjusted. Once the desired prong separation location has been reached, rotation of the cam 900 engages the portion 908 with the prongs 102a, 102b to maintain them against the inner surface 104b.

It should be understood that other cam types and other rotatable mountings can be used, and fall within the scope of the present invention.

FIG. 9d illustrates an end view of the second plate 100b of this second embodiment, showing that the bore 104a has the inner surface 104b.

FIG. 10 illustrates a plan view of the plate assembly 100 of this second embodiment when the prongs 102a, 102b are received within the bore 104a. The prongs 102a, 102b are laterally adjacent one another and when the cam 900 is in the first position (e.g., as shown in FIG. 9a1), the prongs 102a, 102b are not pressed against the inner surface 104b, allowing the prongs 102a, 102b to longitudinally translate freely within the bore 104a through a plurality of positions. Once a desired position of the prongs 102a, 102b is reached, the cam 900 can be slid between the prongs 102a, 102b to the most advantageous position for engaging the prongs 102a, 102b, and can be turned. The turning can be made possible, e.g., by a rotatable mounting of the cam 900 between the prongs 102a, 102b (e.g., the dimensions of the cam 900 discussed above make it possible to rotate the cam 900 between the prongs 102a, 102b, and an engageable feature 904 on the cam 900 that when rotated rotates the cam 900. One example of a suitable engageable feature 904 is a screwdriver-receiving recess as shown. When the cam 900 is turned enough to be placed in the second position (e.g., rotated 90 degrees with respect to the first position as shown in FIG. 9a2), the cam 900 separates the prongs 102a, 102b and presses them against the inner surface 104b, preventing longitudinal translation of the prongs 102a, 102b within the bore 104a, effectively locking the prongs 102a, 102b at the desired position.

With reference again to FIGS. 3c and 3d, in order to enable the plate assembly 100 to at least grossly conform to the cylindrical morphology of the vertebral bodies which it couples, a slight lateral curvature preferably is imparted to the plate assembly 100. More specifically, the first plate 100a has a convex top surface 108a and a concave bottom surface 109a. Similarly, the second plate 100b has a convex top surface 108b and a concave bottom surface 109b and the bore 104a has a corresponding curvature so that it can receive the prongs 102a, 102b of the first plate 100a.

In order to secure the plate assembly 100 to the desired body structure or structures, each plate 100a, 100b includes a feature that can be used to couple the plate 100a, 100b to a body structure. In this embodiment, each feature comprises a pair of through holes. However, it should be understood that in other embodiments, additional or alternative features may be appropriate, including, for example, one or more hooks, rings, recesses, clips, and adhesives.

Accordingly, in this embodiment, with reference again to FIGS. 3a, 3b and 4, a first pair of through holes 110, having internal threading 111, extend fully through the first plate 100a, from the top surface 108a of the plate 100a through to the bottom surface 109a of the plate 100a. A second pair of through holes 112, having internal threading 113, extend fully through the second plate 100b, from the top surface 108b of the plate 100b through to the bottom surface 109b of the plate 109b.

The embodiment shown further includes elements that can be used in conjunction with the features of the plates 100a, 100b to couple the plates 100a, 100b to the body structure. In this embodiment, the elements include screws and cooperative coupling elements. It should be understood that elements or tools other than the ones herein described can alternatively or additionally be used with the described or suggested features of the plates 100a, 100b to couple the plates 100a, 100b to the body structures.

Figure 5:
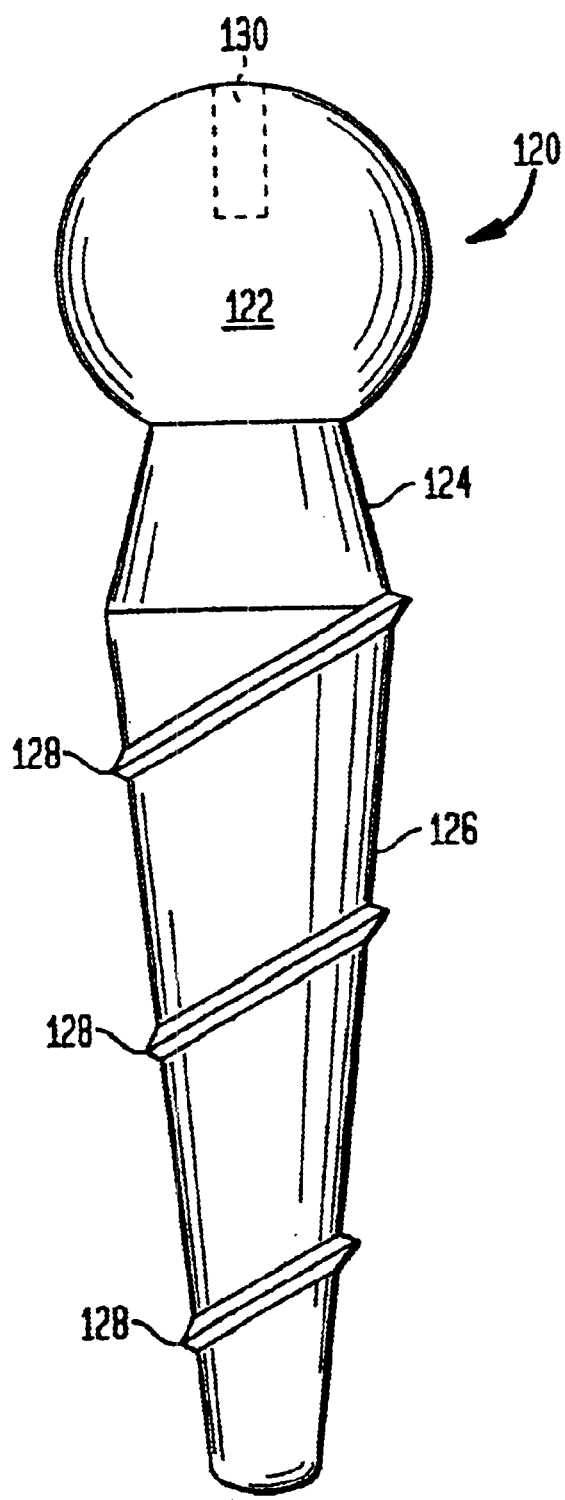
FIG. 5 is a side view of a bone screw of a plate assembly of an embodiment of the invention.

Accordingly, in this embodiment, with reference also to FIG. 5, a screw of a type which is ideally suited for coupling the plates 100a, 100b to vertebral bones is shown in a side view. The screw 120 comprises a head portion 122, a neck 124, and a shaft 126. In FIG. 5, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made by the physician with respect to the conditions of the patient's bone, however, the invention is compatible with a wide variety of shaft designs.

The head portion 122 of the screw 120 is semi-spherical and has a recess 130. It is understood that the semi-spherical shape is necessarily a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 5) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, or most preferably, a hexagonally shaped hole for receiving an alien wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting a coupling element (as described with respect to FIG. 6) to be screwed into the appropriate hole 110 or 112 of the plate assembly 100 and remain coupled to the head 122.

As noted above, this embodiment further includes additional elements that can be used in conjunction with the features of the plates 100a, 100b to couple the plates 100a, 100b to the body structure or structures. Accordingly, referring now also to FIG. 6, a coupling element of the invention is shown in side view, wherein phantom lines show the interior structure of the element along a diametrical cross section. The coupling element 132 comprises a cylindrical socket having an external threading 134. The external threading 134 and the diameter of the exterior of the cylindrical socket is designed to mate with threading 111 or 113 of the holes 110 or 112 of the plate assembly 100, so that the coupling element 132 may be screwed into the plate assembly 100. It is preferable that the uppermost thread 135 be designed to crush-lock the coupling element 132 into the hole 110 or 112. Once screwed into the plate assembly 100, and locked down, the top surface 136 of the coupling element 132 and the respective top surface 108a, 108b of the plate assembly 100 present a flush external surface.

Figure 6:
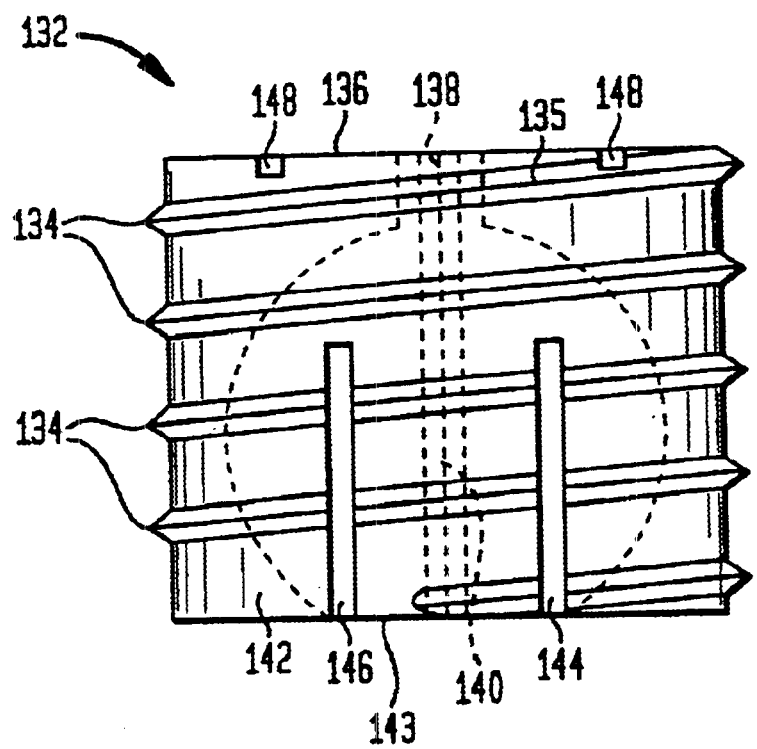
FIG. 6 is a side view of a coupling element of a plate assembly of an embodiment of the invention.

The top surface 136 of the coupling element 132 which is shown in FIG. 6 further comprises a through hole 138, which extends from the top surface 136 to an interior semi-spherical volume 140. This through hole 138 is designed such that the screwdriving tool which is used to insert the screw 120 into the body structure may access and rotate the screw 120 through the coupling element 132.

The interior semi-spherical volume 140 is ideally suited for holding the head 122 of the screw 120, and permitting the screw 120 to rotate through a range of angles. The coupling element 132 has a bottom 142 which has a circular hole (enumerated as 143 on the bottom surface of the side view of the coupling element in FIG. 6) which forms the bottom entrance into the interior semi-spherical volume 140. It is understood that the head 122 of the screw 120 is held within the interior semi-spherical volume 140 by the annular rim, or support lip, 144 of the bottom 142 of the coupling element 132. This annular support lip 144 defines the circular opening 143 which has a diameter less than the diameter of the semi-spherical head 122 of the screw 120.

It is therefore preferred that the lower portion of the coupling element 132 comprise slots 146 so that the physician may insert the head 122 into the interior volume 140. These slots 146 permit the lower portion of the coupling element 132 to expand to accept the inserted head 122, but is secured from releasing the head 122 once the coupling element 132 is screwed into the plate assembly 100. In an alternative variation, the holes 110a or 112a (as shown in phantom in FIG. 7) of the plate assembly 100 are tapered inward with respect to insertion direction. In such a variation, the step of screwing the coupling element 132 into the hole 110a or 112a causes the slots 146 to be compressed and, correspondingly, for the bottom entrance 143 and the annular lip 144 to lock the screw head 122 into position.

In the alternative, it is also possible for the coupling element 132 to be formed in a manner whereby the lower portion does not have to include an expanding entrance 143. In such a variation, the coupling element 132 would necessarily be formed of two separate pieces which would be joined together about the head 122 of the screw 120. In either design, however, it is preferred than the top surface 136 of the coupling element 132 have features, such as holes 148, allowing a second screwdriving tool to easily insert the element 132 into the threaded holes 110, 100a or 112, 112a of the plate assembly 100.

Figure 7:
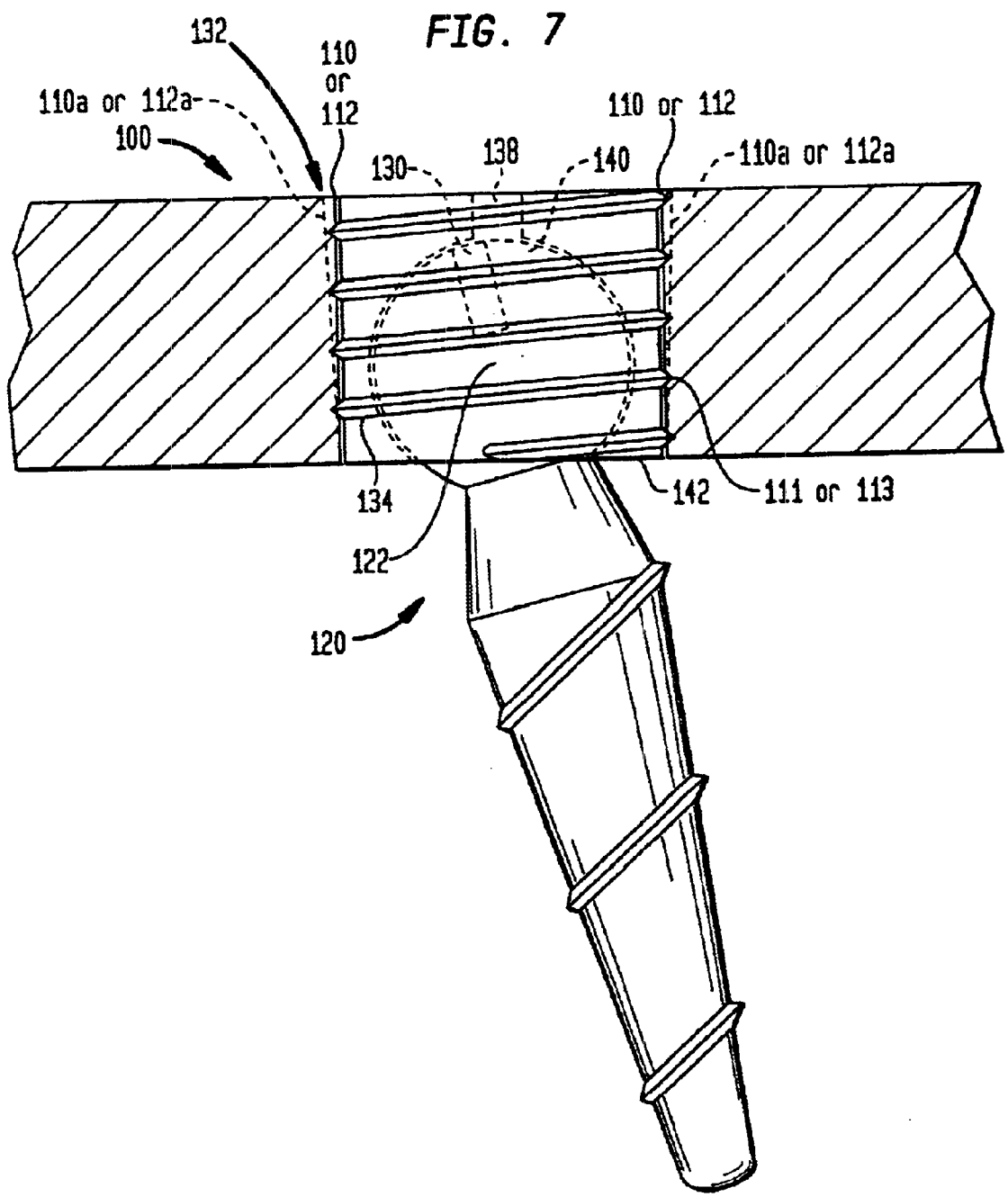
FIG. 7 is a partial side cross sectional view of an assembled embodiment of the invention.

Referring now to FIG. 7, a partial side cross sectional view of a plate assembly 100 of the invention is shown. With reference to the relative positions of the screw 120, plate assembly 100, and coupling element 132, the operative steps of implanting this plate assembly 100 and affixing it to, for example, a pair of vertebral bones, begins with preparing the bones through surgical tissue resection and exposure.

Next, the prongs 102a, 102b of the first longitudinal plate 100a are inserted into the bore 104a of the second longitudinal plate 100b and translated therein until the desired length of the plate assembly 100 is achieved. More specifically, the surgeon determines, after inspection of the vertebral bones to be secured, how far apart the holes 110 of the first longitudinal plate 100a must be spaced from the holes 112 of the second longitudinal plate 100b in order for the plate assembly 100 to be properly coupled to the vertebral bones to be clinically effective.

Once the surgeon makes this determination, he secures the plates 100a, 100b in the selection position by locking the lock assembly. More specifically, with regard to the first embodiment (having the lock assembly shown in FIGS. 3a–d and 4), the surgeon uses a screwdriving tool to rotate the set screw 100e within the threaded bore 100d to advance the set screw 100e until the prongs 102a, 102b separate and press against the inner surface 104b of the bore 104a. The compression of the prongs 102a, 102b against the inner surface 104b secures the position of the plates 100a, 100b relative to one another, thereby fixing the length of the plate assembly 100. It should be noted that preferably, the surgeon is able to use the screwdriving tool to reverse rotate the set screw 100e within the threaded bore 100d to retract the set screw 100e and thereby return the prongs 102a, 102b back together so that they no longer press against the inner surface 104b of the bore 104a so that the prongs 102a, 102b may again freely translate within the bore 104a. This functionality allows the surgeon to readjust the length of the plate assembly 100 if the surgeon's first setting of the length is not correct or is undesirable.

Use of the second embodiment (having the lock assembly shown in FIGS. 9a1, 9a2, 9b, 9c, 9d and 10) by the surgeon is similar in all material respects to use of the first embodiment as noted above, except that locking of the lock assembly involves use of a screwdriving tool to rotate the cam 900 between the prongs 102a, 102b until the prongs 102a, 102b separate and press against the inner surface 104b of the bore 104a. The compression of the prongs 102a, 102b against the inner surface 104b secures the position of the plates 100a, 100b relative to one another, thereby fixing the length of the plate assembly 100. It should be noted that preferably, the surgeon is able to use the screwdriving tool to reverse rotate the cam 900 between the prongs 102a, 102b to return the prongs 102a, 102b back together so that they no longer press against the inner surface 104b of the bore 104a so that the prongs 102a, 102b may again freely translate within the bore 104a. This functionality allows the surgeon to readjust the length of the plate assembly 100 if the surgeon's first setting of the length is not correct or is undesirable.

Once the desired length of the plate assembly 100 is fixed, the plate assembly 100 is positioned against the bones and pre-drill holes are made at the desired insertion angle for the screw 120. Screw 120 and coupling element 132 are then placed together so that the head 122 is within the interior volume 140, whereby the two elements are able to rotate freely with respect to one another, but are nonetheless coupled.

The recess 130 in the screw 120 and the through hole 138 of the coupling element 132 are aligned at first, and an appropriate screwdriving tool is used to insert the screw 120 through the proper hole 110 or 112 (110a or 112a) and into the pre-drilled hole in the bone. Once the screw 120 has been screwed down to the point that the bottom surface of the coupling element 142 contacts the plate 100a or 100b, the first threads 134 of the coupling element are mated to the threading 111 or 113 of the hole 110 or 112 (110a or 112a), respectively.

Complete insertion of the coupling element 132 to the plate assembly 100 preferably locks the element 132 to the plate assembly 100, in addition to locking the screw 120 and plate assembly 100 to the bone. In the variation of the embodiment in which the coupling element 132 has slots (elements 146 of FIG. 6) and an expanding bottom entrance 143, corresponding holes 110 or 112 (110a or 112a) may be tapered; the complete insertion of the coupling element 132 into the hole 110 or 112 therein having the additional benefit of locking the angle of the screw 120.

Figure 8:
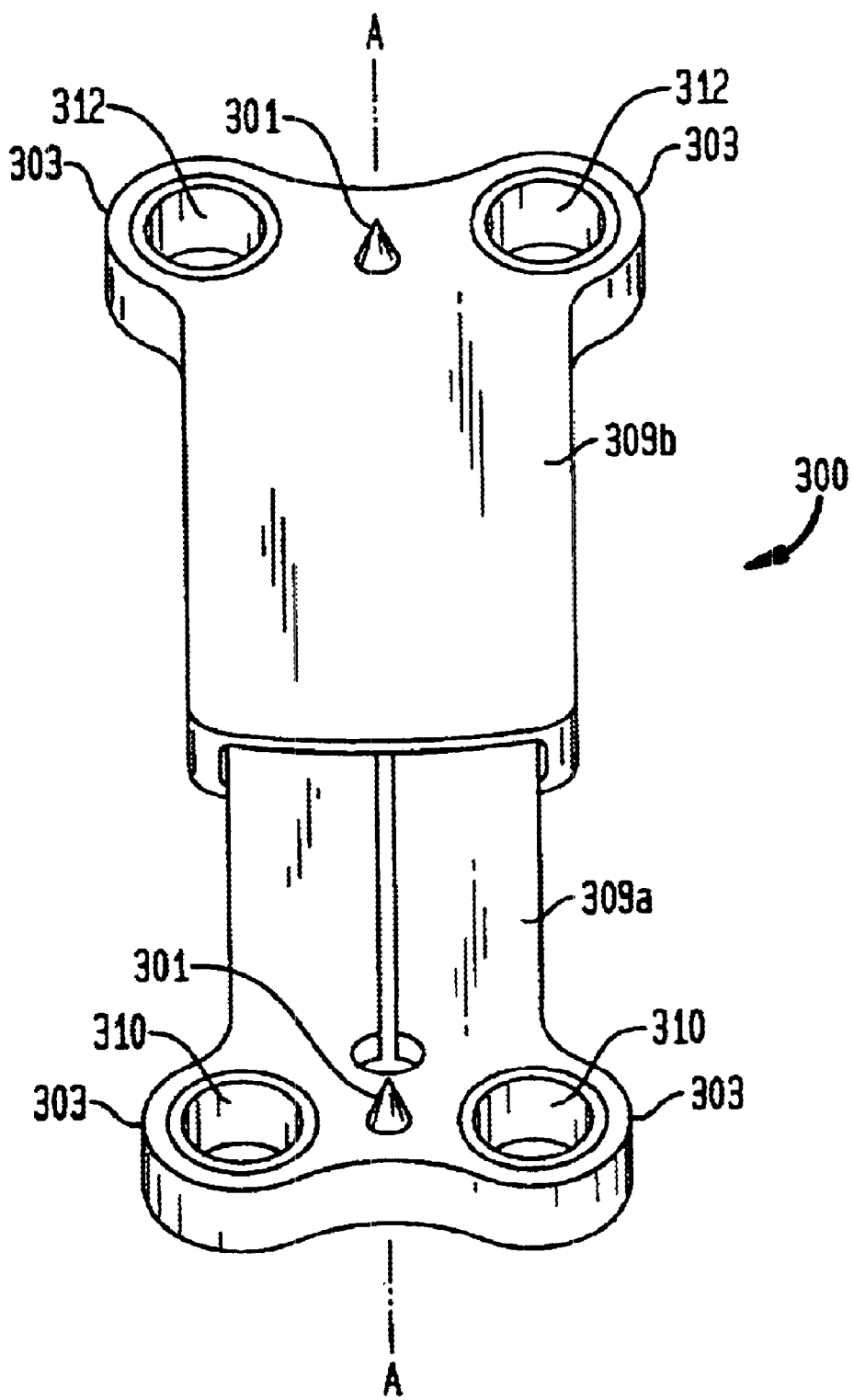
FIG. 8 is a perspective view of a plate assembly of another embodiment of the invention.

Referring now to FIG. 8, a variation of the plate assembly 100 of the invention is shown in perspective view. This plate assembly 300 comprises a first plate 300a corresponding to the first plate 100a of the plate assembly 100 and a second plate 300b corresponding to the second plate 100b of the plate assembly 100. The first plate 300a has through holes 310 and a bottom surface 309a and the second plate 300b has through holes 312 and a bottom surface 309b. The plate assembly 300 further includes at least one feature protruding from one of the bottom surfaces 309a, 309b for removable and temporary fixation of the plate assembly 300 to a vertebral bone. In this embodiment, the feature is a spike. However, it should be understood that other features can additionally or alternatively be used to achieve this functionality without departing from the scope of the invention.

Accordingly, in this embodiment, as shown in FIG. 8, one spike element 301 protrudes from each of the bottom surfaces 309a, 309b. Preferably, each spike 301 is positioned between the pair of holes 310 or 312, on center line A—A. These spikes allow the plate assembly 300 to be temporarily, and easily removably, fixed to vertebral bones during the steps of pre-drilling and insertion of the screws 120 through the holes 310, 312 and into the vertebral bones. This is a desirable operational advantage, as it frees one hand of the surgeon and/or removes extra tools from the surgical site.

It is preferred to have the spikes 301 positioned along the center line A—A for plate assemblies 300 which have a radius of curvature which is equal to or greater than that of the vertebral bodies such as, for example, vertebral bones (i.e., not as curved as the bone). Having the spikes 301 along the center line ensures that the plate assembly 300 can be removably fixed to the bone by simply applying an insertion force against the plate assembly 300 and driving the spikes 301 into the bone. It is understood that for implants wherein the plate assembly 300 has a smaller radius of curvature than the bone, it would be desirable to position the spikes 301 at edges 303 of the plate assembly 300.

While there has been described and illustrated implantation devices for stabilizing and immobilizing regions of the spine by affixing a plate assembly having an adjustable length to the anterior portion of the vertebral bones, it will be apparent to those skilled in the art that variations and modifications are possible without deviating from the broad spirit and principle of the invention which shall be limited solely by the scope of the claims appended hereto.

What is claimed is:

1. A plate assembly, comprising:
   a first plate having an end defined by at least one prong;
   a second plate having a bore, the bore being adapted to receive the at least one prong for translation therein through a plurality of positions, the at least one prong being separable within the bore to lock the at least one prong within the bore at one of the positions.

2. The assembly of claim 1, wherein the bore has an inner surface and the separation of the at least one prong presses the at least one prong against the inner surface.

3. The assembly of claim 1, wherein a lateral curvature is imparted to the plate assembly.

4. The assembly of claim 1, wherein at least one of the plates has a bottom surface and the assembly further comprises at least one feature protruding from the bottom surface for removable and temporary fixation of the plate assembly to a body structure.

5. The assembly of claim 4, wherein the feature comprises a spike.

6. The assembly of claim 1, wherein at least one of the plates comprises a feature that can be used to couple the plate to a body structure.

7. The assembly of claim 6, wherein the feature comprises at least one through hole.

8. The assembly of claim 7, further comprising a bone screw having a shaft that can be inserted into the through hole and into a bone.

9. The assembly of claim 8, further comprising:
a coupling element that has a semi-spherical interior volume and that can be inserted into the through hole; wherein
the screw has a semi-spherical head that can be rotationally freely mounted within the semi-spherical interior volume prior to insertion of the coupling element into the through hole; and wherein
the shaft and the coupling element can be inserted into the through hole and the shaft can be inserted into the bone at a selected angle within a predetermined range of angles, including non-perpendicular angles, relative to a respective one of the plates, thereby locking the coupling element and the head to the respective one of the plates at the selected angle as the head and the coupling element are advanced into the through hole.

10. The assembly of claim 9, wherein:
the head of the screw has a recess to which a screwdriving tool can be mated for inserting the screw into the through hole and into the bone;
the coupling element has a top surface recess through which the screwdriving tool may be inserted; and
the top surface recess can be aligned with the recess in the head of the screw; whereby
the screw can be inserted into the bone using the screwdriver.

11. The assembly of claim 9, wherein:
the interior semi-spherical interior volume is defined by a curved interior surface which forms a receiving socket into which the semi-spherical head is inserted, whereby the head is rotationally freely mounted in the semi-spherical interior volume;
the curved interior surface comprises slots which permit the interior semi-spherical volume to expand to facilitate the insertion of the semi-spherical head of the screw therein; and
the through hole is tapered inwardly to cause, upon insertion of the coupling element into the through hole, the slots to be compressed, which causes the curved interior surface to lock the semi-spherical head of the screw at a definite insertion angle.

12. The assembly of claim 2, wherein said at least one prong includes at least two prongs, the prongs being movable away from one another to effect the separation.

13. The assembly of claim 14, comprising a threaded bore and a set screw passing between the prongs and into the threaded bore.

14. An orthopedic device comprising a longitudinal plate assembly having an adjustable length, the plate assembly including two longitudinal plates;
wherein one of the plates has a longitudinal bore, and the other of the plates has at least one longitudinal prong that is longitudinally translatable within the bore through a plurality of positions for adjusting the length of the plate assembly; and
wherein the at least one prong is separable within the bore at one of the positions to establish the length of the plate assembly.

15. The device of claim 14, wherein a lateral curvature is imparted to the plate assembly.

16. The device of claim 14, wherein the plate assembly has two ends, each of the ends comprising a feature that can be used to couple the end to a body structure.

17. The device of claim 16, wherein at least one of the features comprises a through hole, and wherein the device further comprises:
a bone screw having a head and a shaft that can be inserted into the through hole and into a bone;
a coupling element that has a semi-spherical interior volume and that can be inserted into the through hole; wherein
the head of the screw is semi-spherical and can be rotationally freely mounted within the semi-spherical interior volume prior to insertion of the coupling element into the through hole; and wherein
the shaft and the coupling element can be inserted into the through hole and the shaft can be inserted into the bone at a selected angle within a predetermined range of angles, including non-perpendicular angles, relative to a respective one of the plates, thereby locking the coupling element and the head to the respective one of the plates at the selected angle as the head and the coupling element are advanced into the through hole.

18. The device of claim 14, wherein said at least one prong includes at least two prongs, the prongs being movable away from one another to effect the separable.

19. The device of claim 18, comprising a threaded bore and a set screw passing between the prongs and into the threaded bore.

* * * * *